United States Patent
Zhang et al.

(10) Patent No.: US 11,562,809 B2
(45) Date of Patent: Jan. 24, 2023

(54) METHOD FOR AUTOMATICALLY GENERATING UNIVERSAL SET OF STEREOISOMERS OF ORGANIC MOLECULE

(71) Applicant: SHENZHEN JINGTAI TECHNOLOGY CO., LTD., Guangdong (CN)

(72) Inventors: Huanhuai Zhang, Guangdong (CN); Guangxu Sun, Guangdong (CN); Yang Liu, Guangdong (CN); Shuhao Wen, Guangdong (CN); Jian Ma, Guangdong (CN); Lipeng Lai, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 484 days.

(21) Appl. No.: 16/629,959

(22) PCT Filed: Dec. 25, 2018

(86) PCT No.: PCT/CN2018/123533
§ 371 (c)(1),
(2) Date: Jan. 10, 2020

(87) PCT Pub. No.: WO2020/029521
PCT Pub. Date: Feb. 13, 2020

(65) Prior Publication Data
US 2021/0065850 A1    Mar. 4, 2021

(51) Int. Cl.
*G16C 20/50* (2019.01)
*G06F 30/20* (2020.01)
*G16C 20/00* (2019.01)

(52) U.S. Cl.
CPC ............. *G16C 20/50* (2019.02); *G06F 30/20* (2020.01); *G16C 20/00* (2019.02)

(58) Field of Classification Search
CPC ........ G16C 20/50; G16C 20/00; G16C 20/70; G16C 20/30; G06F 30/20
(Continued)

(56) References Cited

U.S. PATENT DOCUMENTS

2014/0107189 A1*   4/2014   Chakraborty et al. ......................
C07K 14/535
514/44

FOREIGN PATENT DOCUMENTS

| CN | 103984878 | 8/2014 |
| CN | 108763852 | 11/2018 |

OTHER PUBLICATIONS

"International Search Report (Form PCT/ISA/210) of PCT/CN2018/123533," dated Oct. 9, 2019, pp. 1-4.

* cited by examiner

*Primary Examiner* — Thinh T Nguyen
(74) *Attorney, Agent, or Firm* — Muncy, Geissler, Olds & Lowe, P.C.

(57) ABSTRACT

A method for automatically generating a universal set of stereoisomers of an organic molecule. The method includes: (1) segmenting an input molecule into a group of fragments; (2) matching the obtained isomer fragments with fragment templates in a fragment template library; (3) generating all isomers of the corresponding fragments according to fragment template information; and (4) traversing all the isomer fragments and sites thereof, and assembling the fragments at the two ends of a broken bond in the step (1) according to all possible sites of a broken-bond atom to obtain all stereoisomers; and if filtering is needed, performing filtering according to a specified filtering rule.

4 Claims, 5 Drawing Sheets

(58) Field of Classification Search
USPC ............................................................ 703/11
See application file for complete search history.

METHOD FOR AUTOMATICALLY GENERATING UNIVERSAL SET OF STEREOISOMERS OF ORGANIC MOLECULE

CROSS-REFERENCE TO RELATED APPLICATION

This application is a 371 application of International PCT application serial no. PCT/CN2018/123533, filed on Dec. 25, 2018. The entirety of the above-mentioned patent application is hereby incorporated by reference herein and made a part of this specification.

TECHNICAL FIELD

The present invention belongs to the field of organic molecule simulation calculation, and particularly relates to a method for automatically generating a universal set of stereoisomers of an organic molecule. The method is used for comprehensive analysis of chiral, cyclic and cis-trans isomers of molecules, and for generating all stereoisomers except linear isomers, such as isomers formed by rotation of flexible dihedral angles.

DESCRIPTION OF RELATED ART

The generation of stereoisomers is of great significance in cheminformatics. At present, the common generation methods of stereoisomers are mainly knowledge-based methods for generating stereoisomers as follows.

An existing isomer library is usually used to search for a similar structural group with provided stereoisomers. This method is typically performed as follows. A target molecule is to disassembled into fragments on the basis of a known conformation database, and then the same or similar fragments are searched in the database. Finally, the searched fragment isomers are combined into a complete isomer. This method mainly has the following disadvantages: based on the existing knowledge, the fragment isomer coverage of the database is insufficient, and the stereoisomers generated for some molecules are not complete. Especially for cyclic isomers, due to the variety of fused ring forms, it is difficult for existing databases to cover all the cyclic isomer fragments. Therefore, new stereoisomers can not be searched and need to be generated manually.

BRIEF SUMMARY OF THE INVENTION

In view of the above technical problems, the present invention provides a method for automatically generating a universal set of stereoisomers of an organic molecule, to provide as many stereoisomers of common rings as possible.

Specific technical solutions are as follows:

A method for automatically generating a universal set of stereoisomers of an organic molecule, comprising the following steps:

(I) segmenting an input molecule into a group of fragments which are mainly divided into three types: cyclic isomer fragments, cis-trans isomer fragments, and chiral isomer fragments.

(II) matching the obtained isomer fragments with fragment templates in a fragment template library, wherein chiral isomers and cis-trans isomers do not need to be covered by the fragment templates;

(III) generating all isomers of the corresponding fragments according to the fragment template information; and for cis-trans isomers and chiral isomers, exchanging any two sites and performing assembly in step (IV); and (IV) traversing all the isomer fragments and sites thereof, and assembling the fragments at the two ends of a broken bond in the step (I) according to all possible sites of a broken-bond atom to obtain all stereoisomers.

The molecule segmentation method described in step (I) includes the following steps:

(1) if it is determined that the atom is a non-planar atom on the ring, breaking a single bond not on the ring connected to the atom, that is, breaking a non-equivalent substituent connected to the atom; the rule to determine whether the atom is a planar atom on the ring is that: the atom is not connected to a double or triple bond and is not in a conjugated system;

(2) if it is determined that the atom is a chiral center atom, then breaking any single bond connected to the atom, and the single bond, with the smallest atomic order, of a connected atom is typically broken;

(3) if it is determined that the atom is in a cis-trans isomer structure, then breaking any single bond and selecting the single bond of an adjacent atom with a smaller atomic order;

wherein the above-mentioned broken bonds do not include a chemical bond formed with a hydrogen atom.

The specific process of step (II) includes: constructing a graph using an atomic template as a node and a bond template as an edge; and then using a subgraph isomorphic algorithm to perform fragment template matching, wherein the atomic template is a template object describing a group of atoms, the bond template is a template object describing a group of bond types, and the fragment template describes shapes of all stereoisomers of the fragment and all possible sites and relative positions of the sites.

Further, the specific process of assembling the fragments in step (IV) is:

(1) inputting all isomer fragments frg_list;

(2) traversing all the broken bonds, and setting atoms at both ends of the current broken bond as a_atom and b_atom;

(3) finding the fragment containing a_atom or list A containing a_atom and the fragment containing b_atom or list B containing b_atom from the frg_list;

(4) Inserting the list B into all isomer sites of a_atom in the list A, inserting the list A into all isomer sites of b_atom in the list B. Adding a list of new fragments formed by assembling the list A and the list B to the frg_list, and removing the list A and the list B from the frg_list; and (5) if all the broken bonds are not traversed, skipping to step (2).

In the method for automatically generating a universal set of stereoisomers of an organic molecule provided by the present invention, a fragment template only needs to describe the simplest type of fragments, so it is easy to exhaustively list the stereoisomers of common rings. Moreover, the stereoisomers of similar fragments can be described conveniently, the number of the fragments can be greatly reduced, and the construction difficulty of the fragment library can be greatly reduced. By performing fragment segmentation, then traversing all the stereoisomers of the fragments and finally performing combination and assembly according to sites, all the stereoisomers of a molecule can be generated easily.

DETAILED DESCRIPTION OF THE INVENTION

The specific technical solution of the present invention will be described with reference to the embodiments.

Figure 1:
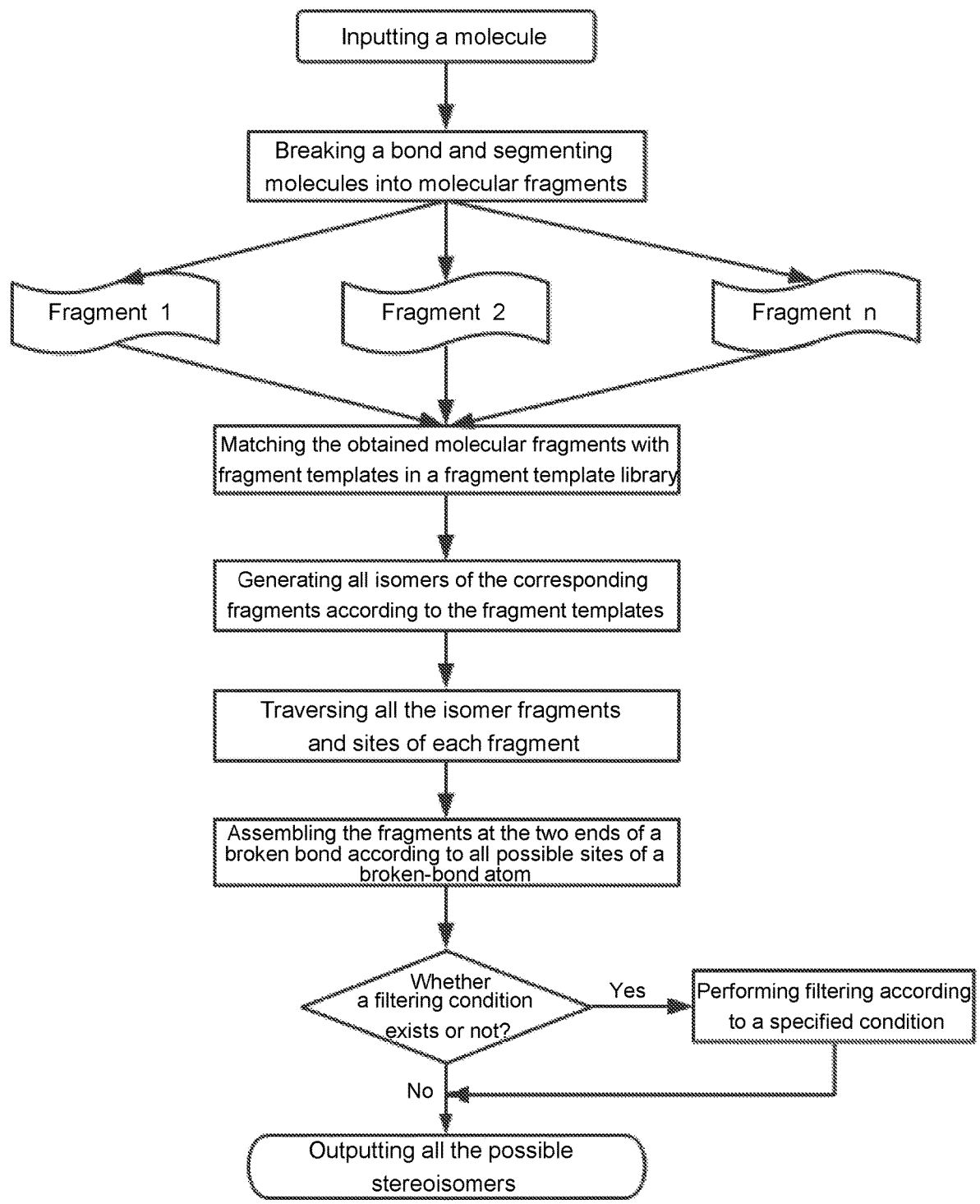
FIG. 1 is a flow chart of the method for generating stereoisomers according to the present invention.

As shown in FIG. 1, a method for automatically generating a universal set of stereoisomers of an organic molecule includes the following steps:

(I) An input molecule is segmented into a group of fragments which are mainly divided into three types: cyclic isomer fragments, cis-trans isomer fragments, and chiral isomer fragments. A cyclic isomer fragment usually includes a non-conjugated ring or a fused ring composed of multiple rings; a cis-trans isomer fragment includes one or more cis-trans sites and the surrounding chemical environment; and a chiral isomer fragment includes a chiral center and surrounding chemical environment. These three types of fragments represent three types of isomers of this molecule, among which the cyclic isomers are the most complicated case.

Figure 6:
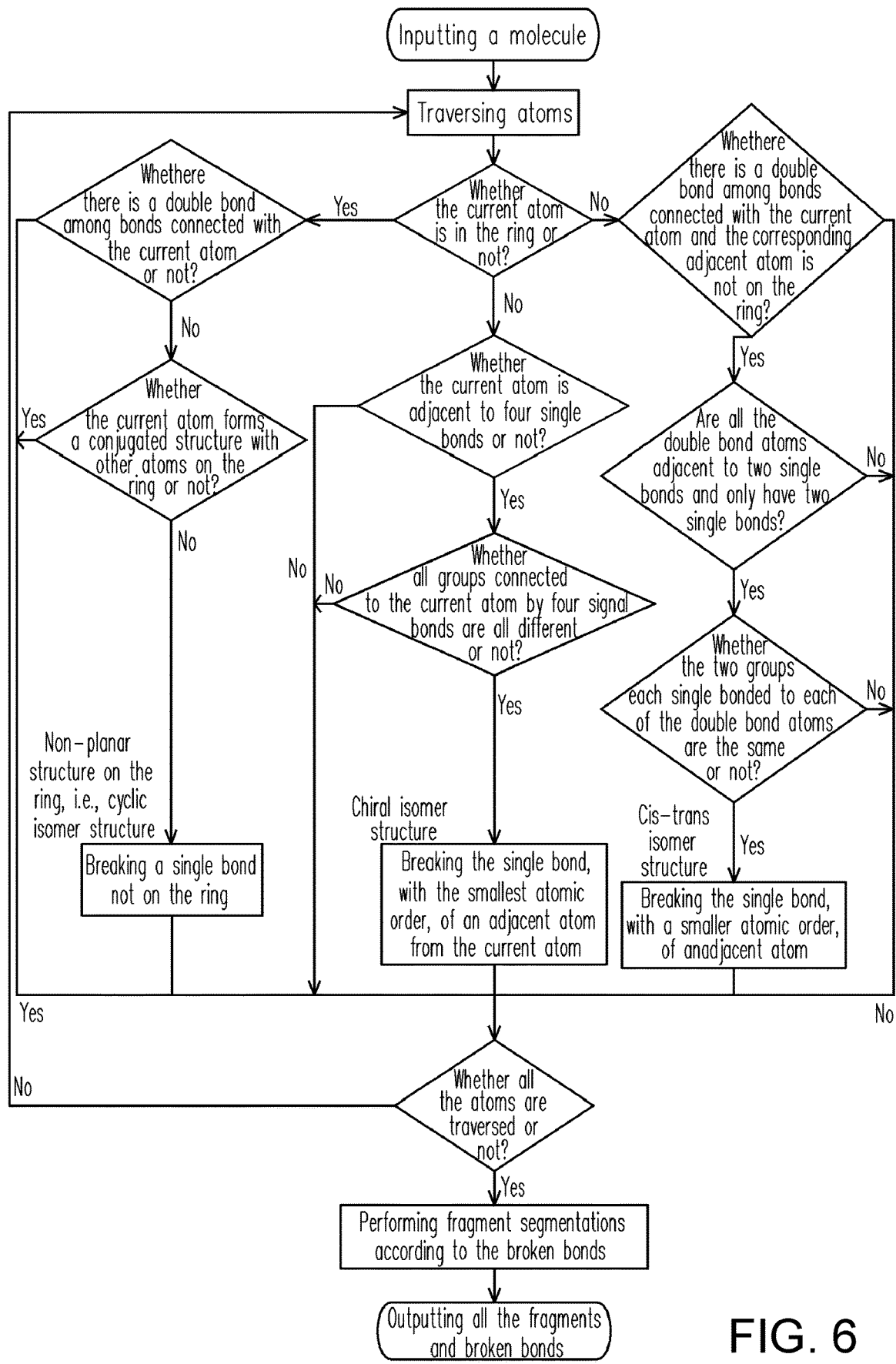
FIG. 6 is a flowchart of molecule segmentation of the present invention.

FIG. 6 shows the calculation flow of molecule segmentation algorithm. The algorithm includes the following processes:

(1) If it is determined that the atom is a non-planar atom on the ring, a single bond not on the ring connected to the atom is broken, that is, a non-equivalent substituent connected to the atom is broken. The rule to determine whether the atom is a planar atom on the ring is that: the atom is not connected to a double or triple bond and is not in a conjugated system.

(2) If it is determined that the atom is a chiral center atom, any single bond connected to the atom is broken, wherein the single bond, with a smallest atomic order, of a connected atom is typically broken.

(3) If it is determined that the atom is in a cis-trans isomer structure, any single bond thereof is broken, and the single bond, with a smaller atomic order, of an adjacent atom is selected herein.

The above-mentioned broken bonds do not include a chemical bond formed with a hydrogen (H) atom or fluorine (F) atom.

Figure 2:
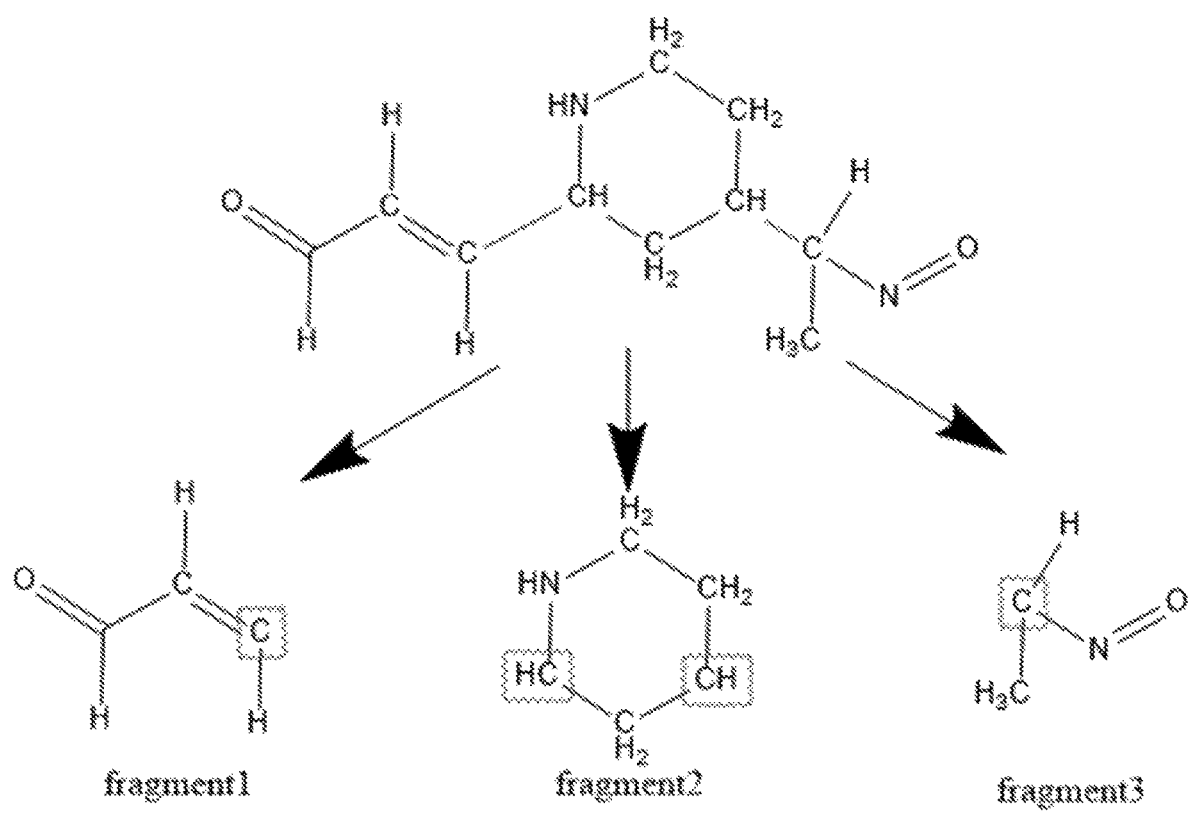
FIG. 2 is a schematic diagram of molecule segmentation according to this embodiment.

The molecule in FIG. 2 is segmented into three fragments: fragment1, which is a cis-trans isomer fragment, fragment2, which is a cyclic isomer fragment, and fragment3, which is a chiral isomer fragment.

Figure 3:
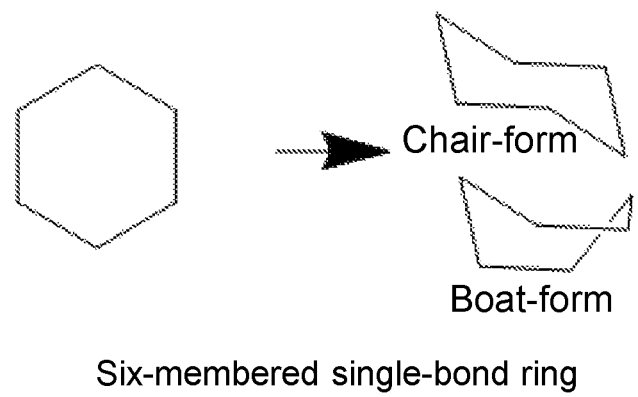
FIG. 3 is a schematic diagram of the isomerization of the six-membered single bond ring in this embodiment to form isomers.
Figure 4:
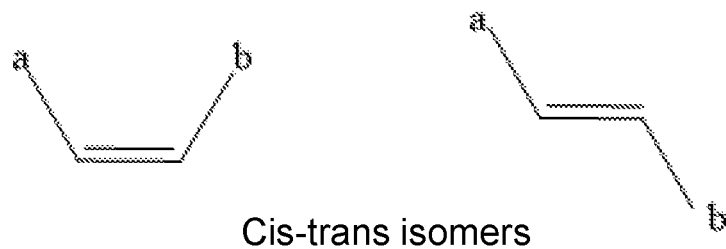
FIG. 4 is a schematic diagram of cis-trans isomerization according to this embodiment to form isomers.
Figure 5:
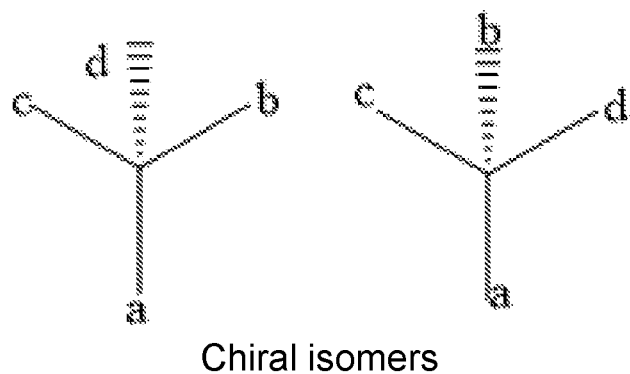
FIG. 5 is a schematic diagram of chiral isomerization according to this embodiment to form isomers.

(II) The obtained isomer fragments are matched with fragment templates in a fragment template library. A graph is constructed using an atomic template as a node and a bond template as an edge; and then a subgraph isomorphic algorithm (generally VF2 algorithm) is used to perform fragment template matching. The atomic template is a template object describing a group of atoms. The bond template is a template object describing a group of bond types. The fragment template describes the shapes of all stereoisomers of the fragment, and all possible sites and the relative positions of the sites. It describes the information of all possible isomers of the same type of fragment: as shown in FIG. 3, it describes a single-bond six-membered ring, which has two stereoisomer forms, i.e., boat-form isomer and chair-form isomer, and each atom on the ring may have two isomer sites. The fragment template describes the simplest fragments, so a fused ring fragment may match multiple fragment templates. The chiral isomers and the cis-trans isomers are very simple and do not need to be covered by templates, as shown in FIG. 4 and FIG. 5, because their chemical nature naturally determines that their isomers can be formed by exchanging any two sites (connected groups or atoms).

(III) All isomers of the corresponding fragments are generated according to the fragment template information. An isomer fragment may match multiple fragment templates. One template corresponds to one ring, so the isomers of a fused ring fragment are all the isomer combinations of all fragment templates corresponding to the fragment. For cis-trans isomers and chiral isomers, assembly is performed by only exchanging any two sites in step (IV).

Figure 7:
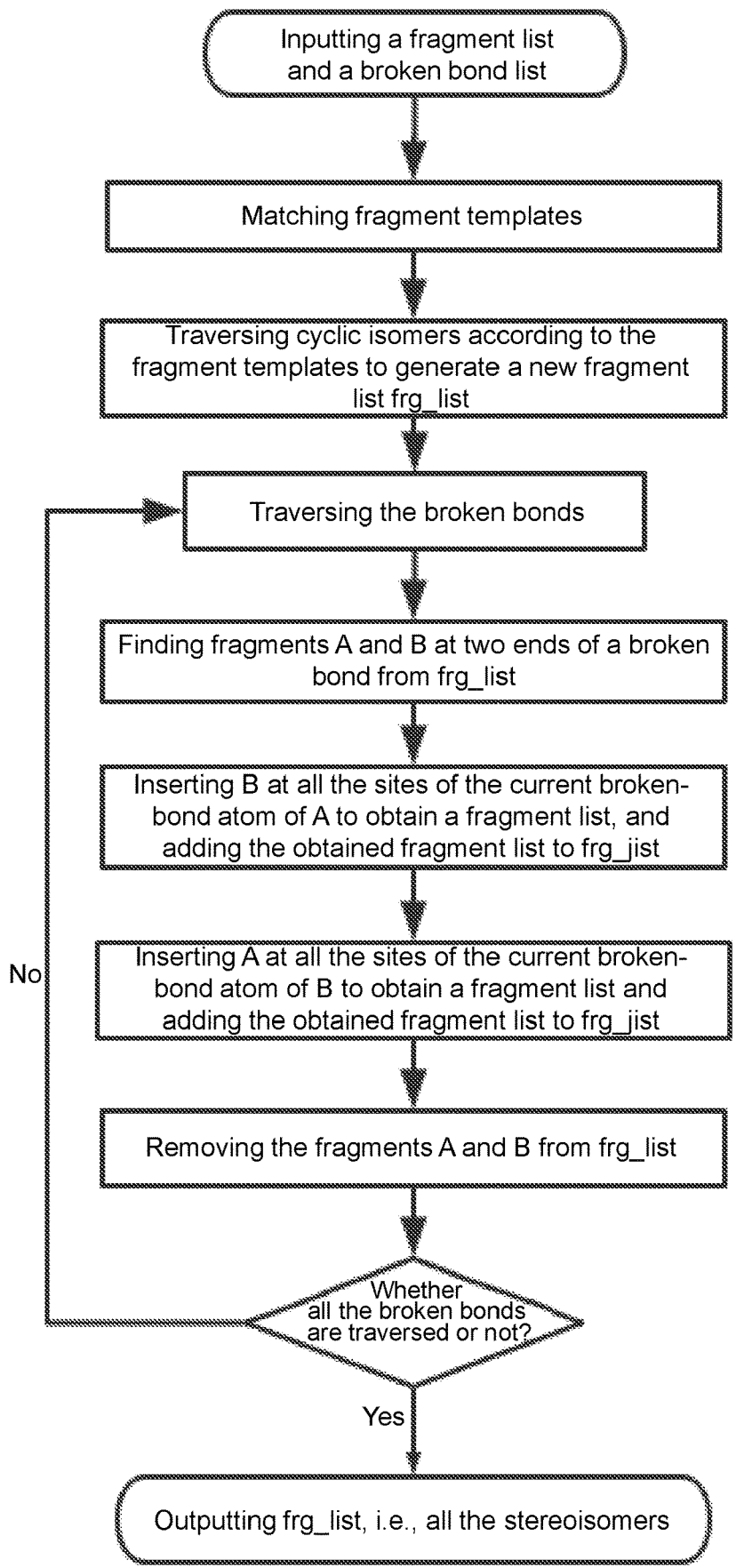
FIG. 7 is a flowchart of fragment assembly according to the present invention.

(IV) All the isomer fragments and sites thereof are traversed, and the fragments at the two ends of the broken bond in the step (I) are assembled according to all possible sites of a broken-bond atom to obtain all stereoisomers. As shown in FIG. 7, the specific process of the fragment assembly is as follows:

(1) inputting all isomer fragments frg_list;

(2) traversing all the broken bonds, and setting atoms at both ends of the current broken bond as a_atom and b_atom;

(3) finding all the fragments containing a_atom from the frag_list and name these fragments as list A, and finding all the fragments containing b_atom from the frag_list and name these fragments as list B;

(4) inserting the list B into all isomer sites of a_atom in the list A, inserting the list A into all isomer sites of b_atom in the list B, adding a list of new fragments formed by assembling the list A and the list B to frg_list, and removing the list A and the list B from the frg_list; and (5) if all the broken bonds are not traversed, skipping to step (2).

The fragment2 segmented from the molecule, as shown in FIG. 2, is a six-membered single-bond ring fragment. This ring has two isomer forms. The two carbon atoms of the broken bond have two isomer sites, so when fragment1, fragment2, and fragment3 are assembled, there are always two insertion sites; therefore, there are 8 (2*2*2) stereoisomers related to fragment2. In addition, fragment1 and fragment3 themselves also have two isomers, so in the end the molecule will generate 32 (8*2*2) stereoisomers in total. If filtering is required, filtering may be performed according to a specified filtering rule.

What is claimed is:

1. A method for automatically generating a universal set of stereoisomers of an organic molecule, comprising the following steps:

(I) segmenting an input molecule into a group of fragments which are mainly divided into three types: cyclic isomer fragments, cis-trans isomer fragments, and chiral isomer fragments;

(II) matching the cyclic isomer fragments with fragment templates in a fragment template library; wherein chiral isomers and cis-trans isomers do not need to be covered by the fragment templates; wherein the fragment templates describe shapes of all stereoisomers of a corresponding fragment and all possible sites and relative positions of the sites; wherein one fragment template corresponds to one ring, so the isomers of a fused ring fragment are all the isomer combinations of all fragment templates corresponding to the fused ring fragment;

(III) generating all isomers of the corresponding fragments according to fragment template information; for cis-trans isomers and chiral isomers, exchanging any two sites of the cis-trans isomers and the chiral isomers and performing assembly in step (IV); and (IV) traversing all the isomer fragments and sites thereof, and assembling the fragments at two ends of a broken bond in the step (I) according to all possible sites of a broken-bond atom to obtain all stereoisomers.

2. The method for automatically generating a universal set of stereoisomers of an organic molecule according to claim 1, wherein the molecule segmentation method described in step (I) comprising the following steps:

(1) if it is determined that an atom is a non-planar atom on the ring, breaking a single bond not on the ring connected to the atom, that is, breaking a non-equivalent substituent connected to the atom; wherein a rule to determine whether the atom is a planar atom on the ring is: the atom is not connected to a double or triple bond and is not in a conjugated system;

(2) if it is determined that the atom is a chiral center atom, then breaking any single bond connected to the atom, wherein the single bond, with a smallest atomic order, of a connected atom is broken;

(3) if it is determined that the atom is in a cis-trans isomer structure, then breaking any single bond and selecting the single bond, with a smaller atomic order, of an adjacent atom;

wherein the above-mentioned broken bonds do not include a chemical bond formed with a hydrogen atom.

3. The method for automatically generating a universal set of stereoisomers of an organic molecule according to claim 1, wherein the specific process of step (II) comprising:

constructing a graph using an atomic template as a node and a bond template as an edge; and then using a subgraph isomorphic algorithm to perform fragment template matching, wherein the atomic template is a template object describing a group of atoms, the bond template is a template object describing a group of bond types.

4. The method for automatically generating a universal set of stereoisomers of an organic molecule according to claim 1, wherein the specific process of assembling the fragments in step (IV) comprising:

(1) inputting a list of all isomer fragments, wherein the list is referred to as frg_list;

(2) traversing all the broken bonds, wherein atoms at both ends of the current broken bond is referred to as a_atom and b_atom;

(3) finding all the fragments containing a_atom from the frg_list, and finding all the fragments containing b_atom from the frg_list, wherein all the fragments containing a_atom is referred to as list A and all the fragments containing b_atom is referred to as a list B;

(4) inserting the list B into all isomer sites of a_atom in the list A, inserting the list A into all isomer sites of b_atom in the list B, adding a list of new fragments formed by assembling the list A and the list B to the frg_list, and removing the list A and the list B from the frg_list; and (5) if all the broken bonds are not traversed, skipping to step (2).

* * * * *